(12) United States Patent
Jain et al.

(10) Patent No.: US 10,842,514 B2
(45) Date of Patent: Nov. 24, 2020

(54) SURGICAL GUIDANCE SYSTEMS, DEVICES, AND METHODS

(71) Applicant: Boston Scientific Limited, St. Michael (BB)

(72) Inventors: Ashish Jain, Uttar Pradesh (IN); Subodh Morey, Goa (IN); Timothy P. Harrah, Cambridge, MA (US); Charudatta Aradhye, Maharashtra (IN); Rajiv Kumar Singh, Maharashtra (IN)

(73) Assignee: Boston Scientific Limited, St. Michael (BB)

( * ) Notice: Subject to any disclaimer, the term of this patent is extended or adjusted under 35 U.S.C. 154(b) by 127 days.

(21) Appl. No.: 16/013,652

(22) Filed: Jun. 20, 2018

(65) Prior Publication Data

US 2018/0368862 A1    Dec. 27, 2018

Related U.S. Application Data

(60) Provisional application No. 62/522,960, filed on Jun. 21, 2017.

(51) Int. Cl.
*A61B 17/22* (2006.01)
*A61B 90/00* (2016.01)
*A61B 90/50* (2016.01)
*A61B 17/34* (2006.01)
*A61B 17/00* (2006.01)

(52) U.S. Cl.
CPC .............. *A61B 17/22* (2013.01); *A61B 17/34* (2013.01); *A61B 17/3403* (2013.01); *A61B 90/39* (2016.02); *A61B 90/50* (2016.02); *A61B 2017/00398* (2013.01); *A61B 2017/00734* (2013.01); *A61B 2017/00876* (2013.01); *A61B 2017/3407* (2013.01); *A61B 2017/3409* (2013.01); *A61B 2090/0807* (2016.02); *A61B 2090/376* (2016.02); *A61B 2090/3966* (2016.02)

(58) Field of Classification Search
CPC ......... A61B 17/22; A61B 90/39; A61B 90/50; A61B 17/34; A61B 17/3403; A61B 2090/0807; A61B 2090/376; A61B 2090/3966; A61B 2017/00398; A61B 2017/00734; A61B 90/30; A61B 90/10; A61B 90/11; A61B 90/35; A61B 2017/3409; A61B 3017/3407
See application file for complete search history.

(56) References Cited

U.S. PATENT DOCUMENTS 5,415,169 A    5/1995  Siczek et al.
6,626,848 B2   9/2003  Neuenfeldt
(Continued)

FOREIGN PATENT DOCUMENTS

EP         1985330 A1    10/2008
WO    WO 2010/017642 A1   2/2010
WO    WO 2015/052719 A1   4/2015

*Primary Examiner* — Katrina M Stransky
(74) *Attorney, Agent, or Firm* — Bookoff McAndrews, PLLC

(57) ABSTRACT

A guidance device may include a base member including a hole extending therethrough. The guidance device may include a handle coupled to the base member. Additionally, a driver may be positioned within the base member and coupled to a shaft extending between the base member and the handle.

20 Claims, 2 Drawing Sheets

(56) References Cited

U.S. PATENT DOCUMENTS

| | | | |
|---|---|---|---|
| 6,689,142 B1 * | 2/2004 | Tremaglio, Jr. ... | A61B 17/3403 604/114 |
| 7,229,401 B2 | 6/2007 | Kindlein | |
| 2002/0111634 A1 | 8/2002 | Stoianovici et al. | |
| 2007/0032741 A1 | 2/2007 | Hibner et al. | |
| 2009/0030339 A1 | 1/2009 | Cheng et al. | |
| 2009/0054835 A1 * | 2/2009 | Anderson ......... | A61M 25/0136 604/95.01 |
| 2010/0042112 A1 * | 2/2010 | Qureshi ............. | A61B 17/3403 606/130 |

\* cited by examiner

SURGICAL GUIDANCE SYSTEMS, DEVICES, AND METHODS

CROSS-REFERENCE TO RELATED APPLICATIONS

This patent application claims the benefit of priority under 35 U.S.C. § 119 to U.S. Provisional Patent Application No. 62/522,960, filed Jun. 21, 2017, which is herein incorporated by reference in its entirety.

TECHNICAL FIELD

Aspects of the present disclosure generally relate to medical devices and procedures. In particular, some aspects relate to surgical guidance systems, devices, and methods.

BACKGROUND

Non-invasive surgical procedures enable a medical professional to treat an internal area of a body while minimizing a size of a physical opening on the exterior skin of the body. Many non-invasive procedures are designed to treat a particular area of the body, such as an organ. Percutaneous nephrolithonomy (or "PCNL"), for example, is one such procedure, wherein an object, such as a needle, is inserted through the skin and into a kidney for removal of a kidney stone. Precise placement and advancement of the needle is required to avoid damaging the kidney or surrounding tissues. Therefore, medical imaging techniques, such as fluoroscopy, may be used in PCNL procedures to locate a kidney, track the location of the needle with respect to the kidney, and to facilitate aligning the needle at a desired angle to avoid inadvertent injury to tissues in or surrounding the kidney.

Additionally, once an appropriate angle of access has been determined, medical professionals typically grasp a proximal end (e.g., an end opposite a puncturing tip) of the needle and apply a pushing or advancing force to puncture the skin and advance the needle through patient tissue and into a target location (e.g., a target calyx) within a kidney. However, application of a pushing or advancing force on a proximal end of the needle may cause the needle to bow outwardly (e.g., away) from a needle axis, potentially interfering with the proper orientation or angle of insertion of the needle. Additionally, as a needle is advanced, the needle will experience varying degrees of resistance from tissue. For example, typically the needle passes through relatively harder tissue (e.g., tissue having a firm intercellular matrix) and then through relatively softer tissue (e.g., tissue having a looser intercellular matrix). As such, an amount or degree of pushing force needed to advance the needle through the relatively hard tissue is greater than the amount or degree of pushing force needed to advance the needle through the relatively soft tissue. Due to the change in hardness of tissue, medical professionals must be careful to timely adjust the amount of pushing force so as to avoid inadvertently passing through the soft tissue and injuring the ureteropelvic junction and/or surrounding vessels.

The systems, devices, and methods of the current disclosure may rectify or lessen some of the challenges described above, and/or address other aspects of the prior art.

SUMMARY

Aspects of the present disclosure relate to, among other things, systems, devices, and methods for surgical guidance. Each of the aspects disclosed herein may include one or more of the features described in connection with any of the other disclosed aspects.

In one example, a guidance device may include a base member including a hole extending therethrough. The guidance device may include a handle coupled to the base member. Additionally, a driver may be positioned within the base member and coupled to a shaft extending between the base member and the handle.

Examples of the guidance device may include one or more of the following features. The base member may include a radiopaque member extending about a circumference of the hole of the base member. The radiopaque member may be a radiopaque ring. The handle may be coupled to an actuator rotatable with respect to the handle. The actuator may extend proximally of the handle, may be coupled to the shaft, and may be rotatable about a longitudinal axis of the shaft. The shaft may be coupled to a motor disposed within the handle. A speed selector may be operably coupled to the motor. A mode selector may be configured to move relative to the handle between a forward indicia, a neutral indicia, and a reverse indicia. When the mode selector is aligned with the forward indicia, actuation of the motor may result in rotation of the shaft in a first direction. When the mode selector is aligned with the reverse indicia, actuation of the motor may result in rotation of the shaft in a second direction. A battery operably coupled to the motor. A distal end of the shaft may include a shaft gear. The driver may include a first shaft having a first gear including teeth configured to mesh with teeth of the shaft gear. The driver may include a pair of rollers and each roller may include a channel therein. The shaft may include a first portion and a second portion, and in a first configuration, the first portion may be coupled with the second portion, and in a second configuration, the first portion may be detached from the second portion.

In a further example, a method may include positioning a base member of a guidance device at a location on skin of a patient. The method may further include rotating a shaft extending between a handle of the guidance device and the base member of the guidance device. Also, the method may include rotating a pair of rollers so as to move an insertion device toward the skin of the patient and through a hole of the base member.

Examples of the method may include one or more of the following features. The method may include confirming a location of the base member via a radiopaque member positioned on the base member. Rotating the shaft may include actuating a motor operably coupled to the shaft. The method may further include adjusting a direction of rotation of the shaft.

In a further example, a guidance device may include a base member including a hole extending therethrough. The guidance device may further include a radiopaque ring extending around the hole of the base member. Additionally, a driver may be positioned within the base member and coupled to a shaft extending between the base member and a handle. The driver may include a pair of rollers.

Examples of the guidance device may include on or more of the following features. The shaft may include a first portion and a second portion, and, in a first configuration, the first portion may be coupled with the second portion, and, in a second configuration, the first portion may be detached from the second portion. The shaft may be coupled to a motor disposed within the handle. A speed selector may be operably coupled to the motor.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

Examples of the present disclosure relate to surgical guidance systems, devices, and methods for treating internal areas of a subject's body. Such a surgical guidance system may include a base and at least one insertion device associated with the base for insertion into an organ (e.g., a kidney) of a patient via a puncture in the skin of the patient. Additionally, such a surgical guidance system may facilitate controlled advancement of the insertion device into tissue of a patient.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative and directional positions of the components of an exemplary base or insertion device. When used herein, "proximal" refers to a position closer to the exterior of the body of the patient or closer to an operator and/or medical professional using the base or insertion device. In contrast, "distal" refers to a position farther away from the operator and/or medical professional using the base or insertion device, or closer to the interior of the body of the patient.

While aspects of the present disclosure are described in reference to a surgical guidance system in conjunction with medical imaging technology to track a position of an insertion device (e.g., needle) relative to a kidney of a patient, the disclosure is not so limited. Rather, any reference to a particular type of medical procedure (e.g., PCNL), insertion device (e.g., needle), area of the treatment (e.g., kidney), or medical imaging technology (e.g., fluoroscopy) is provided for convenience and not intended to limit the present disclosure. Accordingly, the exemplary surgical guidance systems, devices, and methods described herein may be utilized for or with any other appropriate procedure, insertion device, area of treatment, or imaging technology, medical or otherwise. For example, other energy emitting devices similar to fluoroscopes may be suitable for use with devices and methods according to the present disclosure. Additionally, although some of the arrangements described herein refer to only radiopaque materials for use as an imaging reference material, other types of imaging reference materials may be used in connection with other imaging systems (such as ultrasound, MRI, or CAT-scan devices).

Figure 1:
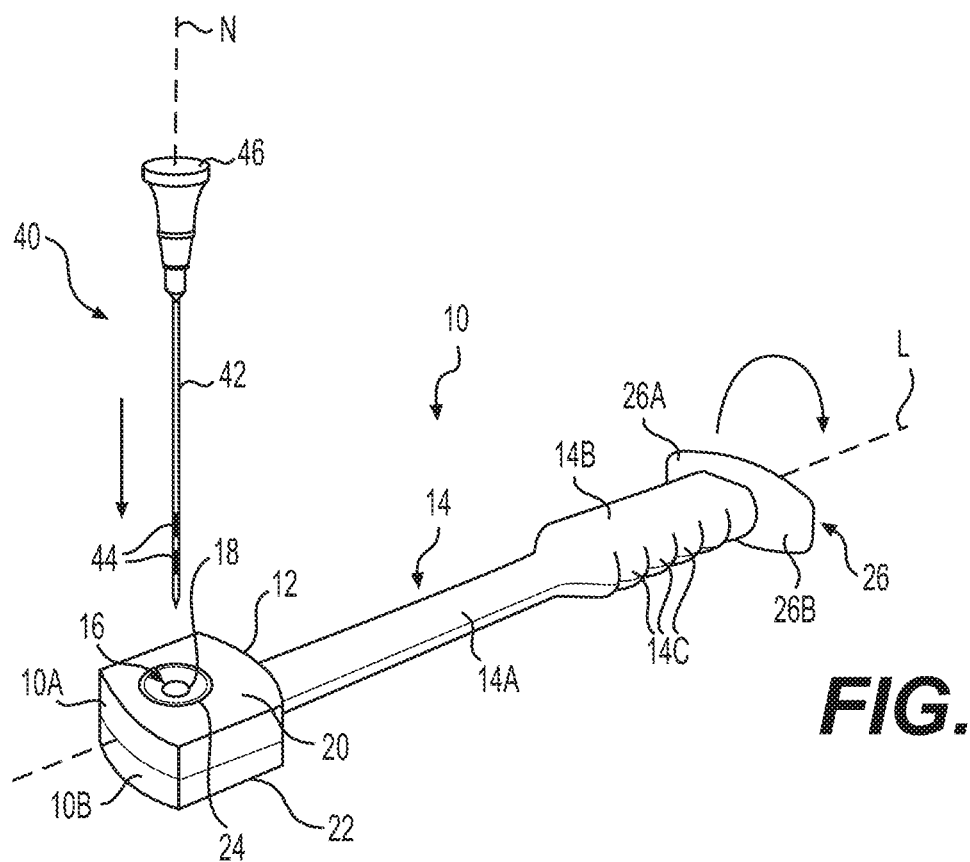
FIG. 1 illustrates an exemplary guidance system including a base and an insertion device, according to an aspect of the present disclosure.

As shown in FIG. 1, a surgical guidance system comprises a base 10 extending along a longitudinal axis L. Base 10 includes a base member 12 and a handle 14 coupled to (or integrally formed with) base member 12. As shown in FIG. 1, base member 12 may be generally rectangular shaped and have a dimension (e.g., width extending in a direction perpendicular to longitudinal axis) greater than a dimension (e.g., width or diameter) of handle 14. In other arrangements, however, base member 12 may have any appropriate shape (e.g., square, circular, oval, triangular, polygonal, irregular shapes, and/or combinations thereof). Additionally, in other arrangements, base member 12 may have a dimension (e.g., width) smaller than or the same as a dimension (e.g., width or diameter) of handle 14. Additionally, base 10 may be a clam-shell arrangement in which two halves of base 10 (e.g., a top or first half 10A and a bottom or second half 10B) are coupled to one another to form base 10.

As also shown in FIG. 1, base member 12 includes a through hole 16. Through hole 16 extends between a first opening 18 on a first surface 20 (on first half 10A) of base member 12 and a second opening (not shown in the orientation of FIG. 1) on a second surface 22 (on second half 10B) of base member 12, opposite of first surface 20. First opening 18 may be tapered, conical, or otherwise funnel-shaped so as to facilitate passage of an insertion device 40 therethrough. A silicone, rubber, semi-rigid or elastomeric material may line or be included in, or an walls of, through hole 16 so as to frictionally engage insertion device 40. Alternatively, through hole 16 may have a diameter sufficiently similar in size to a diameter of a portion of insertion device 40 extending therethrough so as to frictionally grip insertion device 40. In either arrangement, insertion device 40 may be securely positioned within through hole 16, and may be advanced as will be further described below.

Base member 12 includes radiopaque member 24 on, or in a groove in, first surface 20. For example, radiopaque member 24 may include a ring or wire of radiopaque material extending circumferentially about (e.g., surrounding) first opening 18. In some arrangements, however, radiopaque member 24 may extend about less than the entire circumference of first opening 18. Additionally, in some arrangements, radiopaque member 24 may be discontinuous about all or some of the circumference of first opening 18. In some arrangements, radiopaque member 24 may be a first radiopaque member, and base 10 may include a second radiopaque member (not shown) on second surface 22. Such a second radiopaque member may include a ring or wire of radiopaque material extending circumferentially about (e.g., surrounding) the second opening (not shown). In some arrangements, however, the second radiopaque member may extend about less than the entire circumference of the second opening. Additionally, in some arrangements, the second radiopaque member may be discontinuous about the circumference of the second opening. The second radiopaque member may include one or more of the features described above in connection with first radiopaque member 24.

As shown in FIG. 1, handle 14 may have a varied dimension including a first portion 14A and a second portion 14B, which may be enlarged relative to first portion 14A to facilitate grasping by the medical professional. In some arrangements, second portion 14B may include one or more ribs, channels, or other such geometric features 14C to ensure a secure grip of second portion 14B by the medical professional. Base member 12 may be positioned at a first end of handle 14 while an actuator 26 may be positioned at a second end, opposite the first end, of handle 14. Actuator 26 is rotatable about longitudinal axis L (e.g., in one or both of a clock-wise and a counter-clock-wise direction) so as to rotate a shaft 28 (FIG. 2) to thereby actuate a driver 30 (FIG. 2), as will be described in further detail below. Accordingly, actuator 26 may have any shape or arrangement so as to facilitate grasping by a medical professional. For example, as shown in FIG. 1, actuator may have a curved shape such that a medical professional may wrap his/her hand around actuator 26, thereby positioning a first portion of their hand (e.g., an index finger) around a first portion 26A of actuator 26 and a second portion of their hand (e.g., a middle, ring, and/or pinky finger) around second portion 26B of actuator 26. In use, a medical professional may grasp second portion 14B of handle with a first hand (e.g., the medical professional's non-dominant hand) while wrapping a second hand (e.g., the medical professional's dominate hand) around actuator 26. Once so positioned, the medical professional may rotate actuator 26 about longitudinal axis L so as to rotate shaft 28 (FIG. 2), to actuate driver 30 (FIG. 2), as will be described in further detail below.

An exemplary insertion device 40 is illustrated in FIG. 1 as having an elongated body or shaft 42 extending along axis N. Insertion device 40 may be any type of elongated object, such as a needle, a cannula, a catheter with one or more working channels, a rigid or flexible tube, or like element. In some arrangements, insertion device 40 may be an 18 or 21 gauge insertion needle having a lumen extending therethrough. A distal end of insertion device may have a sharpened or angled tip configured or arranged to facilitate penetration of bodily tissue (e.g., into and/or through the skin of a patient). At least a portion of insertion device 40 includes a radiopaque material to enhance visualization of insertion device 40 via fluoroscopy. For example, in some arrangements, the entirety of shaft 42 may be radiopaque, while in other arrangements, one or more portions of shaft 42, such as band(s) 44, may be radiopaque. A proximal end of insertion device has a hub or interface 46 having one or more of a polygonal shape, circular, triangular, or spherical shape. In some aspects, interface 46 may be coupled with a syringe (not shown) or the like for aspiration and/or injection of fluid (e.g., urine), as will be described in further detail below.

Figure 2:
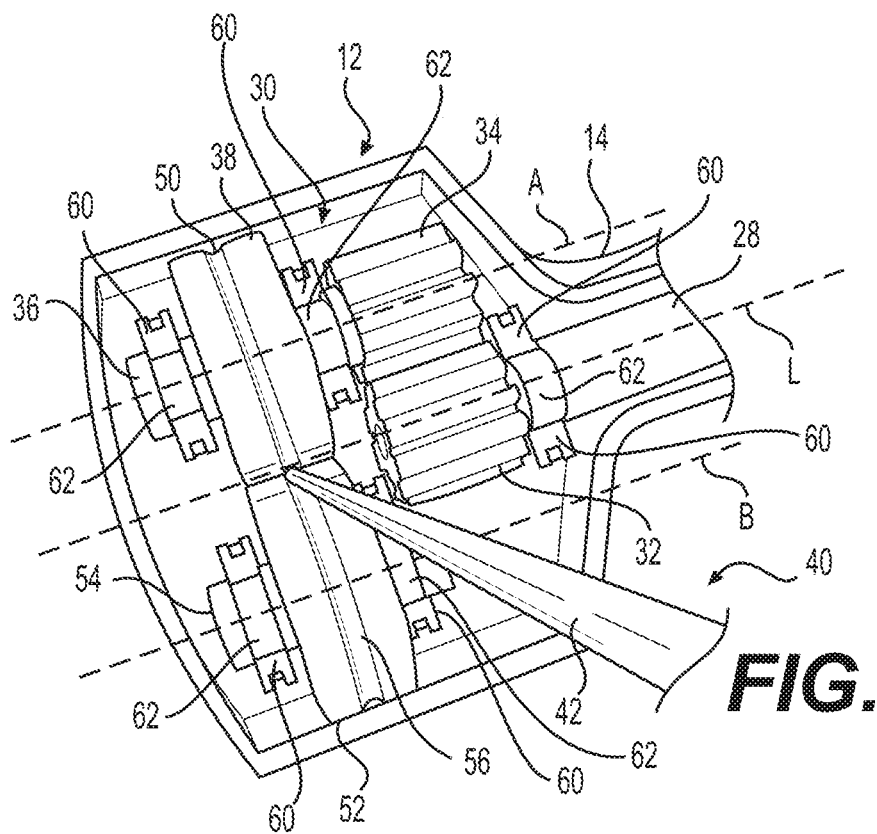
FIG. 2 illustrates a driver of the guidance system of FIG. 1, according to a further aspect of the present disclosure.

FIG. 2 is a view of base member 12 having first portion 10A removed so as to provide a view of driver 30. As shown, driver 30 includes a gearing system to transfer rotational motion of shaft 28 into linear motion to advance or retract insertion device 40. For example, a distal end of shaft 28 terminates in a first gear or drive gear 32. Drive gear 32 includes a plurality of teeth to mesh, engage, interlock, or otherwise cooperate with teeth of a shaft gear 34. Shaft gear 34 is coupled to a first shaft 36 such that rotation of shaft gear 34 results in likewise rotation of first shaft 36. Also, a first roller 38 is coupled to or mounted on first shaft 36. First roller 38 includes an insertion device groove or channel 50 sized so as to receive shaft 42 of insertion device 40. As shown, a second roller 52 is coupled to or mounted on a second shaft 54 of driver 30. Similar to first roller 38, second roller 52 includes an insertion device groove or channel 56 sized so as to receive shaft 42 of insertion device 40. Each of channels 50 and 56 may include a silicone, rubber, compressible, semi-rigid or elastomeric material so as to frictionally engage insertion device 40 and ensure a secure grip on shaft 42 of insertion device 40.

As shown, shaft 28 has a central longitudinal axis collinear with longitudinal axis L while a central longitudinal axis of each of first shaft 36 and second shaft 54 are non-collinear with longitudinal axis L. Rather, a central longitudinal axis A of first shaft 36 and a central longitudinal axis B of second shaft 54 are parallel with each other, and parallel with longitudinal axis L. In other words, first shaft 36 and second shaft 54 are disposed on opposite sides of longitudinal axis L. Additionally, each of shaft 28, first shaft 36, and second shaft 54 is received within at least one support 60 so as to maintain an axial alignment of the respective shaft. For example, a distal end portion of shaft 28 is received within a support 60. Although not shown, a proximal end portion of shaft 28 may likewise be received within a support 60. Additionally, each of first shaft 36 and second shaft 54 may be received within a pair of supports 60 disposed on opposite sides of a respective roller 38 and 52, as shown in FIG. 2. In such a manner, each of shaft 28, first shaft 36, and second shaft 54 may be maintained in proper axial alignment along longitudinal axis L, central longitudinal axis A, and a central longitudinal axis B, respectively. As shown, each of shaft 28, first shaft 36, and second shaft 54 may include a support groove 62. Each support groove 62 may include a narrowed or thinned portion of a respective one of shaft 28, first shaft 36, and second shaft 54 within which a respective one of supports 60 may be received. In some arrangements, a lubricious material may be positioned on one, both, or between supports 60 and support grooves 62 to reduce friction therebetween.

Figure 3:
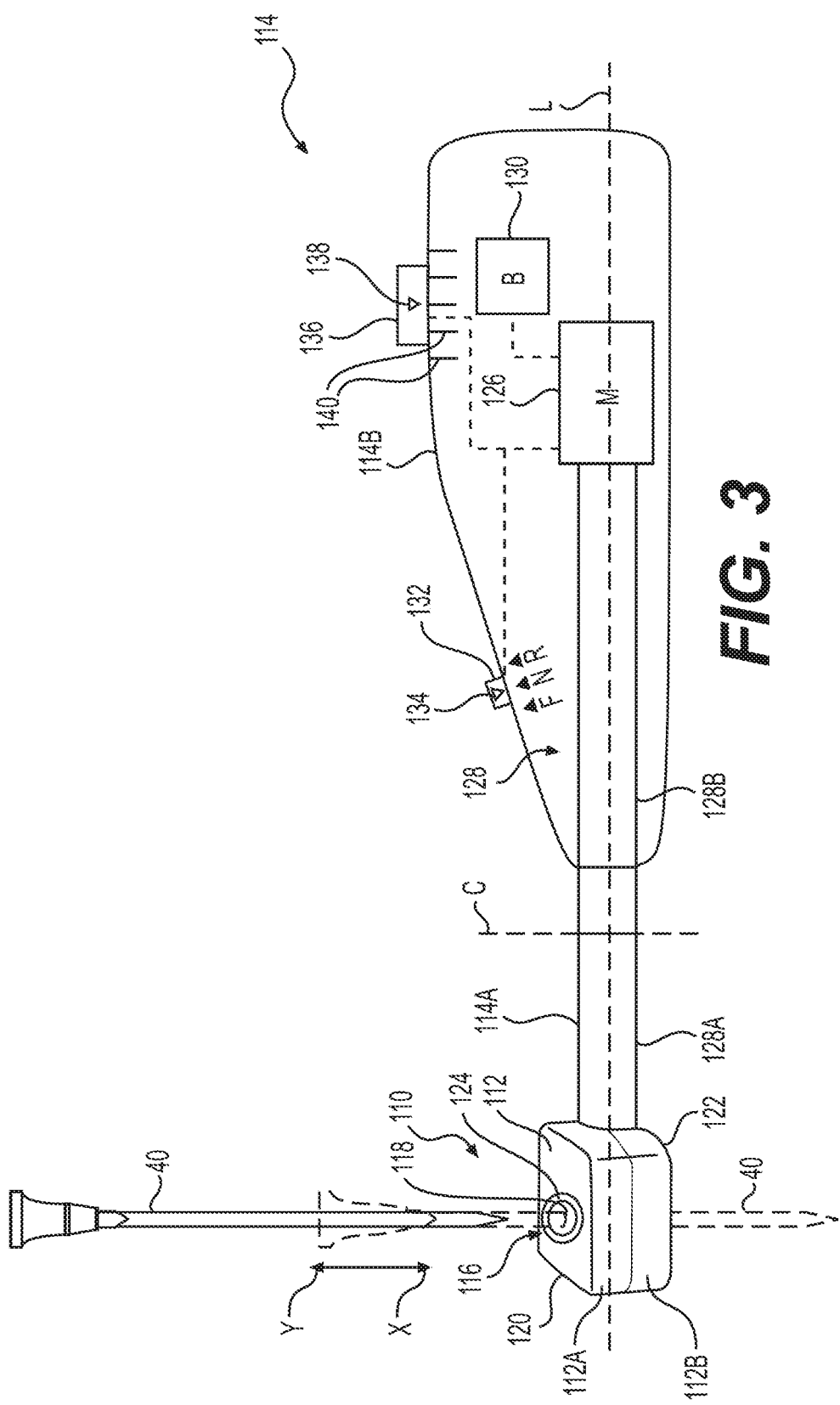
FIG. 3 illustrates an additional exemplary guidance system including a base and an insertion device, according to a further aspect of the present disclosure.

A surgical guidance system according to a further arrangement is shown in FIG. 3. The system of FIG. 3 is similar to the system of FIG. 1, but with mechanical actuator 26 replaced with a motor 126 coupled to shaft 128. As shown, the system includes a base 110 extending along a longitudinal axis L. Base 110 includes a base member 112 and a handle 114 coupled to the base member 112. Base member 112 may be similarly shaped and constructed as base member 112, described above. Additionally, base member 112 includes a through hole 116 extending between a first opening 118 on a first surface 120 (on a first half 112A of base member 112) and a second opening (not shown in the orientation of FIG. 3) on a second surface 122 (on second half 112B of base member 112), opposite of first surface 120. First opening 118 may be tapered, conical, or otherwise funnel-shaped so as to facilitate passage of an insertion device 40 therethrough. A silicone, rubber, semi-rigid or elastomeric material may line or be included in through hole 116 so as to frictionally engage insertion device 40. Alternatively, through hole 116 may have a diameter sufficiently similar in size to a diameter of a portion of insertion device 40 extending therethrough so as to frictionally grip insertion device 40. In either arrangement, insertion device 40 is securely positioned within through hole 116, and may be advanced as will be further described below.

Base member 112 includes radiopaque member 124 on first surface 120. For example, radiopaque member 124 may include a ring or wire of radiopaque material extending circumferentially about (e.g., surrounding) first opening 118. Additionally, in some arrangements, radiopaque member 124 may be discontinuous about the circumference of first opening 118. In some arrangements, radiopaque member 124 may be a first radiopaque member, and base 110 may include a second radiopaque member (not shown) on second surface 122. Such a second radiopaque member may include a ring or wire of radiopaque material extending circumferentially about (e.g., surrounding) the second opening (not shown). In some arrangements, however, the second radiopaque member may extend about less than the entire circumference of the second opening and/or be discontinuous about the circumference of the second opening.

As shown in FIG. 3, handle 114 may have a first portion 114A and a second portion 114B which is enlarged relative to first portion 114A to facilitate grasping by the medical professional. First portion 114A may be selectively uncoupled from second portion 114B along axis C. For example, following completion of a procedure, a medical professional may disconnect, uncouple, or otherwise disengage first portion 114A from second portion 114B such that second portion 114B may be sterilized and reused for a further procedure. In such an arrangement, first portion 114A and second portion 114B may be threadably coupled via corresponding screw threads (not shown) on first portion 114A and second portion 114B. As such, rotation of second portion 114B in a first direction (e.g., clock-wise) about longitudinal axis L and relative to first portion 114A may securely couple first portion 114A and second portion 114B. Additionally, rotation of second portion 114B in a second direction (e.g., counter-clock-wise) about longitudinal axis L and relative to first portion 114A may uncouple first portion 114A from second portion 114B.

Further, shaft 128 includes a first portion 128A and second portion 128B. First portion 128A and second portion 128B may be magnetically coupled to one another such that, upon coupling of first portion 114A to second portion 114B of handle 114, first portion 128A and second portion 128B of shaft 128 may be brought into contact with one another. Due to magnetic attraction between first portion 128A and second portion 128B, rotation of second portion 128B via motor 126 will result in likewise rotation of first portion 128A, thus resulting in rotation of gears and shafts of driver 30 (described in connection with FIG. 2) housed within base member 112 to advance or retract shaft 42 of insertion device 40. Alternatively, connection of first portion 128A and second portion 128B of shaft 128 may occur in any other appropriate fashion such as, a threaded (e.g., screw) coupling, dove-tail, key-fit, interference fit, or the like without departing from the scope of this disclosure.

A proximal end of shaft 128, e.g., second portion 128B, may be coupled with motor 126 for rotation therewith. Motor 126 is additionally connected to a power source 130. Power source 130 may be an internal battery (e.g., a rechargeable or disposable battery) and/or a power adapter so as to provide an electrical connection to a wall outlet (not shown). In either arrangement, power source 130 may provide sufficient power to drive motor 126 so as to rotate shaft 128 and drive driver 30 (FIG. 2). Alternatively, motor 126 may be replaced with any other appropriate drive mechanism such as, for example, pneumatic actuators, hydraulic actuators, or the like.

As shown in FIG. 3, handle 114 further includes direction selector 132 having an indicator 134 and a speed selector 136 having an indicator 138. Each of the direction selector 132 and speed selector 136 is in communication with motor 126. Direction selector 132 is movable between three indicia, an insertion device advancement (e.g., forward) indicia F, a neutral or stopped indicia F, and an insertion device retraction (e.g., reverse) indicia R. In use, the medical professional may apply a force to urge or retract direction selector 132 relative to handle 114 so as to align indicator 134 with one of forward indicia F, neutral indicia N, or reverse indicia R. When indicator 134 is advanced toward indicia F, direction selector 132 delivers a signal to motor 126 to drive shaft 128 in a first direction (e.g., clock-wise) so as to actuate driver 30 to advance distally or insert insertion device 40 through the skin and towards a target calyx of a kidney of the patient (e.g., in direction X towards the arrangement shown in phantom in FIG. 3). In contrast, when indicator 134 is withdrawn toward indicia R, direction selector 132 delivers a signal to motor 126 to drive shaft 128 in a second direction (e.g., counter-clock-wise) so as to actuate driver 30 to retract or withdraw insertion device 40 proximally away from skin and the target calyx of the kidney of the patient (e.g., in direction Y, and as shown in solid unbroken lines in FIG. 3). When indicator 134 is moved so as to align with indicia N (as shown in FIG. 3), direction selector 132 delivers a signal to motor 126 to stop, halt, or prevent rotation of shaft 128 in either of the first direction X or second direction Y.

Speed selector 136 is movable between a plurality of indicia 140 indicative of a speed of rotation of motor 126. For example, each progressively distal indicia 140 of the plurality of indicia is indicative of a higher speed of rotation of motor 126. For example, a proximal-most indicia 140 may be indicative of a slowest speed of motor 126, while a distal-most indicia 140 may be indicative of a fastest speed of motor 126. Indicia 140, between the proximal-most and distal-most indicia 140, may indicate a progressively increasing speed between the slowest and fastest speeds of motor 126. For example, each of indicia 140 between the proximal-most and distal-most indicia 140 may be equidistantly spaced so as to indicate equal increases in speed of motor 126. In other aspects, however, indicia 140 may be non-equidistantly spaced to indicate non-equal increases in speed between adjacent indicia 140. Accordingly, to increase or decrease a speed of motor 126, the medical professional may advance or retract speed selector 136 so as to align indicator 138 with a desired one of indicia 140, thereby sending a signal from speed selector 136 to motor 126 to adjust or maintain a desired speed of rotation. In some aspects, speed selector 136 can advance a pre-determined distance. Such as, e.g., 0.5 mm, 1 mm, 2 mm, 5 mm, etc.

As shown schematically in FIG. 3, each of selectors 132 and 136 includes a slider arrangement. However, the disclosure is not so limited. Rather, any one or both of selectors 132 and 136 may alternatively or additionally include a knob, wheel, or depressible member/push button (not shown). For example, in some arrangements, speed selector 136 may be a depressible member such that an increase in a depressing force applied to speed selector 136 may signal an increased speed of motor 126.

In use, a medical professional may use any of base 10 or base 110 to align insertion device 40 with a desired treatment location, e.g., a target calyx of a kidney. Optionally, prior to or during a procedure (e.g., a PCNL procedure), the patient may be directed to ingest a radiopaque contrast dye. Alternatively, one or more portions or structures of the patient, e.g., a target calyx in a kidney, may be injected with radiopaque contrast dye. In such a manner, the target calyx or other structure can be visualized via fluoroscopy.

Next, the medical professional may move base 10 and/or base 110 relative to the skin of the patient (e.g., over the torso and/or sides of the patient). For example, the medical professional may translate, slide, or otherwise move second surface 22 or 122 of base member 12 or 112, respectively, along the skin of a patient so as to position base 10 or 110 (and thereby, insertion device 40) at a preferred angle into the target calyx. In order to confirm the proper angle has been achieved, a medical professional, with the aid of a fluoroscopy device, may view one or more radiopaque portions of base 10, base 110, insertion device 40, and the target calyx. For example, the medical professional may observe the location of radiopaque member 24 or 124 relative to the insertion device 40 and target calyx. Once the radiopaque member 24, and/or 124 is in line with axis N of insertion device 40 and the target calyx, the proper insertion angle is identified.

Upon confirming an appropriate angle of insertion of insertion device 40, the medical professional may rotate a C-arm of the fluoroscopy device to an angle perpendicular to the angle at which it was positioned when the angle of insertion of insertion device 40 was identified. In such an orientation, the fluoroscopy device enables a clear view of the depth of insertion of insertion device 40. Following confirmation of the angle of insertion and rotation of the C-arm of the fluoroscopy device, insertion device 40 may be advanced (e.g., moved distally along axis N) through through hole 16 and/or 116 to penetrate the skin of the patient and advance a tip of insertion device 40 to a target location within the body of the patient (e.g., a target calyx). To do so, a medical professional may grasp and rotate actuator 26 relative to handle 14 in a first direction (e.g., clock-wise) (FIG. 1) or align indicator 134 of direction selector 132 with forward indicia F and align indicator 138 of speed selector 136 with one of the plurality of indicia 140 so as to select a desired speed (FIG. 3). In either manner, shaft 28 or 128 is consequently rotated so as to actuate insertion device 40 driver 30 to advance insertion device 40. That is, rotation of shaft 28 or 128 results in likewise rotation of shaft gear 34, first shaft 36, first roller 38, second shaft 54, and second roller 52, as described above in connection with FIG. 2. Upon rotation of first roller 38 and second roller 52, insertion device 40 is advanced through through hole 16 and into or towards the patient skin. If it is determined to be necessary or desired to withdraw insertion device 40, a medical professional may grasp and rotate actuator 26 relative to handle 14 in a second direction (e.g., counter-clock-wise) (FIG. 1) or align indicator 134 of direction selector 132 with reverse indicia R and align indicator 136 of speed selector 136 with one of the plurality of indicia 140 so as to select a desired speed (FIG. 3). In either manner, shaft 28 or 128 is consequently rotated so as to actuate driver 30 to withdraw insertion device 40.

A proper depth of insertion of insertion device 40 may be confirmed in any appropriate manner, e.g., via visualization of one or more radiopaque portions (e.g., bands 44) of insertion device 40, visual confirmation of urine coming through the needle, aspiration of urine through a syringe connected to the needle, or some combination of the above. A guidewire may be inserted through the shaft 42 and the shaft 42 may be removed over the guidewire. The guidewire may be left to guide instruments necessary to the PCNL procedure into the target calyx, such as dilating catheters, access sheaths, lithotripsy devices, retrieval devices and the like.

As noted above, speed selector 136 may be adjusted to alter (e.g., increase or decrease) a speed of rotation of shaft 128, and consequently, a speed of insertion or withdrawal of insertion device 40. In some arrangements, for example, a total depth of insertion of insertion device may be about 12 cm. The first 10 cm may be traversed at a faster or increased speed, while the final 2 cm may be traversed at a lower or reduced speed. That is, the medical professional may first align indicator 138 of speed selector 136 with a first indicia 140 and advance insertion device 40 a distance of 10 cm. Next, the medical professional may align indicator 138 of speed selector 136 with a second indicia 140, positioned proximally of the first indicia 140, and advance insertion device 40 a distance of 2 cm. In such a manner, a medical professional may controllably advance insertion device 40. It is understood that above example is merely explanatory and not restrictive of the methods described herein.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

We claim:

1. A guidance device, comprising:
   a base member including a hole extending therethrough;
   a handle coupled to the base member; and
   a driver positioned within the base member and coupled to a shaft extending between the base member and the handle,
   wherein the shaft extends proximally from the driver and through at least a portion of the handle, and the shaft is configured to rotate about a longitudinal axis of the shaft to actuate the driver.

2. The guidance device of claim 1, wherein the base member includes a radiopaque member extending about a circumference of the hole of the base member.

3. The guidance device of claim 1, wherein the handle is coupled to an actuator rotatable with respect to the handle.

4. The guidance device of claim 3, wherein the actuator extends proximally of the handle, is coupled to the shaft, and is rotatable about a longitudinal axis of the shaft.

5. The guidance device of claim 1, wherein the shaft is coupled to a motor disposed within the handle.

6. The guidance device of claim 5, further including a speed selector operably coupled to the motor.

7. The guidance device of claim 5, further including a mode selector being moveable relative to the handle between a forward indicia, a neutral indicia, and a reverse indicia.

8. The guidance device of claim 7, wherein, when the mode selector is aligned with the forward indicia, actuation of the motor results in rotation of the shaft in a first direction.

9. The guidance device of claim 7, wherein, when the mode selector is aligned with the reverse indicia, actuation of the motor results in rotation of the shaft in a second direction.

10. The guidance device of claim 1, wherein a distal end of the shaft includes a shaft gear, and wherein the driver includes a first shaft having a first gear including teeth configured to mesh with teeth of the shaft gear.

11. The guidance device of claim 1, wherein the driver includes a pair of rollers, each roller including a channel therein.

12. The guidance device of claim 1, wherein the shaft includes a first portion and a second portion, wherein, in a first configuration, the first portion is coupled with the second portion, and wherein, in a second configuration, the first portion is detached from the second portion.

13. A method, comprising:
    positioning a base member of a guidance device at a location on skin of a patient;
    rotating a shaft extending between a handle of the guidance device and the base member of the guidance device, wherein the shaft is rotated about a longitudinal axis of the handle to actuate a driver positioned within the base member; and rotating a pair of rollers of the driver so as to move an insertion device toward the skin of the patient and through a hole of the base member.

14. The method of claim 13, further including confirming a location of the base member via a radiopaque member positioned on the base member.

15. The method of claim 13, wherein the rotating the shaft includes actuating a motor operably coupled to the shaft.

16. The method of claim 13, further including adjusting a direction of rotation of the shaft.

17. A guidance device, comprising:
a base member including a hole extending therethrough;
a radiopaque ring extending around the hole of the base member; and
a driver positioned within the base member and coupled to a shaft extending between the base member and a handle, wherein the driver includes a pair of rollers,
wherein the handle is coupled to the base member, and the handle extends proximally from the base member.

18. The guidance device of claim 17, wherein the shaft includes a first portion and a second portion, wherein, in a first configuration, the first portion is coupled with the second portion, and wherein, in a second configuration, the first portion is detached from the second portion.

19. The guidance device of claim 17, wherein the shaft is coupled to a motor disposed within the handle.

20. The guidance device of claim 19, further including a speed selector operably coupled to the motor.

\* \* \* \* \*